(12) United States Patent
Landis

(10) Patent No.: US 11,009,146 B2
(45) Date of Patent: May 18, 2021

(54) SEALING VALVE FOR A SENSOR

(71) Applicant: Teledyne Detcon, Inc., Thousand Oaks, CA (US)

(72) Inventor: Jeffrey Lynn Landis, Charlotte, NC (US)

(73) Assignee: Teledyne Detcon, Inc., Thousand Oaks, CA (US)

(*) Notice: Subject to any disclaimer, the term of this patent is extended or adjusted under 35 U.S.C. 154(b) by 0 days.

(21) Appl. No.: 16/435,646

(22) Filed: Jun. 10, 2019

(65) Prior Publication Data

US 2019/0293203 A1 Sep. 26, 2019

Related U.S. Application Data

(63) Continuation of application No. 15/125,731, filed as application No. PCT/US2014/027926 on Mar. 14, 2014, now Pat. No. 10,316,984.

(51) Int. Cl.
*G01L 19/14* (2006.01)
*F16K 24/04* (2006.01)
(Continued)

(52) U.S. Cl.
CPC ............ *F16K 31/20* (2013.01); *F16K 24/046* (2013.01); *F16K 31/18* (2013.01); *G01D 11/245* (2013.01);
(Continued)

(58) Field of Classification Search
CPC ........ G01F 15/005; G01F 15/10; G01F 15/14; G01F 22/02; G01F 23/0038;
(Continued)

(56) References Cited

U.S. PATENT DOCUMENTS 323,992 A * 8/1885 Wilcox ............... G01L 19/0007
73/756
1,854,094 A * 4/1932 Aschenbach ............. G01L 7/04
73/707
(Continued)

FOREIGN PATENT DOCUMENTS

GB 1 260 132 A 1/1972
GB 1260132 A ‡ 1/1972 ............. G01F 23/56
(Continued)

OTHER PUBLICATIONS

PCT Written Opinion of the International Preliminary Examining Authority dated Nov. 21, 2014, for corresponding International Application No. PCT/US2014/027926 International Filing Date: Mar. 14, 2014 consisting of 10 pages.‡

*Primary Examiner* — Hailey K. Do
(74) *Attorney, Agent, or Firm* — Christopher & Weisberg, P.A.

(57) ABSTRACT

A sealing valve is provided for a sensor that includes a sensing element and a sensor opening that exposes the sensing element. The sealing valve includes a housing that is configured to be mounted to the sensor such that an internal channel of the housing fluidly communicates with the sensor opening. The sealing valve includes a float element configured to float along a surface of the liquid. The float element is configured to move within the internal channel between an open position and a closed position. The float element is configured to close the sensor opening to the internal channel in the closed position. The sensor opening is open to the internal channel when the float element is in the open position. The float element is configured to rise with the surface of the liquid within the internal channel toward the closed position.

10 Claims, 4 Drawing Sheets

(51) Int. Cl.
*G01D 11/24* (2006.01)
*G01L 19/06* (2006.01)
*G01F 15/08* (2006.01)
*F16K 31/22* (2006.01)
*G01F 15/14* (2006.01)
*F16K 31/20* (2006.01)
*F16K 31/18* (2006.01)

(52) U.S. Cl.
CPC ............ *G01L 19/147* (2013.01); *F16K 31/22* (2013.01); *G01F 15/08* (2013.01); *G01F 15/14* (2013.01); *G01L 19/0654* (2013.01)

(58) Field of Classification Search
CPC .... G01F 23/0053; G01F 23/14; G01F 23/164; G01F 23/30; G01F 23/56; G01F 15/08; F16K 24/02; F16K 24/04; F16K 24/042; F16K 24/044; F16K 24/046; F16K 24/06; F16K 31/18; F16K 31/20; F16K 31/22; F16K 31/24; F16K 31/26; F16K 37/0066; F16K 37/0075; F16K 37/0091; F16L 37/28; F16L 37/37; F16L 37/248; F16L 55/055; Y10T 137/053; Y10T 137/2808; Y10T 137/2965; Y10T 137/3068; Y10T 137/3099; Y10T 137/6004; Y10T 137/7423; Y10T 137/7426; Y10T 17/7436; Y10T 137/8158; Y10T 137/8326; Y10T 137/8342; Y10T 137/0874; G01L 19/0654; G01L 19/147; G01D 11/245
See application file for complete search history.

(56) References Cited

U.S. PATENT DOCUMENTS

| | | | | | |
|---|---|---|---|---|---|
| 1,878,947 | A | * | 9/1932 | Luff | F16K 33/00 137/433 |
| 2,223,509 | A | ‡ | 12/1940 | Brauer | E21B 21/10 137/433 |
| 2,296,189 | A | * | 9/1942 | Rudolf | G01F 23/42 73/321 |
| 4,116,586 | A | ‡ | 9/1978 | Forney | F01B 25/02 137/101.27 |
| 4,270,560 | A | * | 6/1981 | Kearney | F16K 17/16 116/268 |
| 4,945,947 | A | ‡ | 8/1990 | Westra | F16K 15/04 137/51 |
| 4,991,615 | A | ‡ | 2/1991 | Szlaga | B60K 15/03519 137/202 |
| 5,358,009 | A | ‡ | 10/1994 | Cambell | B67D 7/002 137/209 |
| 5,466,020 | A | * | 11/1995 | Page | F16L 37/252 285/361 |
| 5,687,756 | A | ‡ | 11/1997 | VanNatta | B60K 15/03519 137/202 |
| 5,960,819 | A | * | 10/1999 | Weissinger | B60K 15/03519 137/315.11 |
| 6,058,970 | A | ‡ | 5/2000 | Osaki | B60K 15/03504 137/141 |
| 6,082,392 | A | ‡ | 7/2000 | Watkins, Jr. | B67D 7/002 137/312 |
| 6,530,396 | B1 | * | 3/2003 | Frey | F16K 1/307 137/557 |
| 7,624,756 | B1 | * | 12/2009 | Coogle | F24F 13/222 137/240 |
| 8,869,627 | B2 | ‡ | 10/2014 | Al-Hadhrami | G01F 1/74 73/861.04 |
| 8,934,263 | B2 | ‡ | 1/2015 | Eckhardt | H01R 12/585 361/784 |
| 2005/0121076 | A1 | ‡ | 6/2005 | Engle | A01J 7/00 137/205 |
| 2006/0000511 | A1 | ‡ | 1/2006 | Shade | F16K 15/04 137/53 |
| 2010/0170794 | A1 | ‡ | 7/2010 | Gibson | G01N 27/4062 204/406 |
| 2011/0126610 | A1 | ‡ | 6/2011 | Sekiya | G01N 27/4077 73/25 |
| 2011/0315235 | A1 | ‡ | 12/2011 | Colefax | B60C 23/0408 137/22 |
| 2013/0306157 | A1 | * | 11/2013 | Aylon | E03B 7/07 137/1 |
| 2016/0298779 | A1 | * | 10/2016 | Heiman | E03F 5/08 |

FOREIGN PATENT DOCUMENTS

| | | | | |
|---|---|---|---|---|
| GB | 1 407 537 A | | 9/1975 | |
| GB | 1407537 A | ‡ | 9/1975 | .......... F16K 24/042 |
| GB | 1 410 742 A | | 10/1975 | |
| GB | 1410742 A | ‡ | 10/1975 | .......... G01F 23/185 |
| WO | WO-2008104967 A2 | * | 9/2008 | ............. G01F 23/72 |
| WO | 2014/008255 A1 | | 1/2014 | |
| WO | WO-2014008255 A1 | ‡ | 1/2014 | ........ G01N 33/0009 |

\* cited by examiner
‡ imported from a related application

SEALING VALVE FOR A SENSOR

CROSS-REFERENCE TO RELATED APPLICATION

This Application is a continuation of and claims priority to U.S. patent application Ser. No. 15/125,731 filed Sep. 13, 2016, entitled "SEALING VALVE FOR A SENSOR" which claims priority to International Application No. PCT/US2014/027926, filed Mar. 14, 2014, entitled "SEALING VALVE FOR A SENSOR", the entireties of both of which are incorporated herein by reference

BACKGROUND

The subject matter disclosed herein relates generally to sensors, more particularly to protecting sensors from exposure to a liquid.

Environmental sensing systems may include a variety of sensors for detecting the presence and/or concentration of various chemicals in various environments. For example, sensors may be used in hazardous environments for detecting the presence and/or concentration of hazardous (e.g., volatile, combustible, and/or toxic) gases.

At least some known sensors are used in environments where the sensor is exposed to one or more liquids. For example, sensors used in and/or around sump areas, holding areas, wells, and/or the like may be exposed to ground water and/or other liquids such as corrosive liquids, toxic liquids, acidic liquids, combustible liquids, fuels, petroleum based liquids, oils, and/or the like. A sensing element of the sensor may be exposed to the liquid when the surface level of the liquid rises to the height of the sensor and immerses the sensor. Splatter, waves, and/or other motion of the liquid are other examples of exposure of the sensing element to the liquid.

Exposure to the liquid may damage the sensing element of the sensor, which may cause the sensor to malfunction and/or fail. Accordingly, exposure to liquids may increase the maintenance, repair, and/or replacement costs of operating an environmental sensing system. Moreover, exposure to liquids may decrease the reliability of an environmental system when a sensor fails to detect the presence of a hazardous gas within a hazardous environment.

BRIEF DESCRIPTION

In an embodiment, a sealing valve is provided for a sensor that includes a sensing element and a sensor opening that exposes the sensing element. The sealing valve includes a housing having an internal channel. The housing is configured to be mounted to the sensor such that the internal channel fluidly communicates with the sensor opening of the sensor. The housing includes a housing opening that fluidly communicates with the internal channel for enabling a liquid to enter the internal channel. The sealing valve includes a float element configured to float along a surface of the liquid. The float element is held in the internal channel of the housing such that the float element is configured to move within the internal channel between an open position and a closed position. The float element is configured to close the sensor opening to the internal channel in the closed position. The sensor opening is open to the internal channel when the float element is in the open position. The float element is configured to rise with the surface of the liquid within the internal channel toward the closed position.

In an embodiment, a sealing valve is provided for a sensor that includes a sensing element and a sensor opening that exposes the sensing element. The sealing valve includes a housing having an internal channel. The housing is configured to be mounted to the sensor such that the internal channel fluidly communicates with the sensor opening of the sensor. The housing includes a housing opening that fluidly communicates with the internal channel for enabling a liquid to enter the internal channel. The sealing valve includes a float element configured to float in the liquid. The float element is held in the internal channel of the housing such that the float element is configured to move within the internal channel toward and away from the sensor opening. The float element is configured to rise with the surface of the liquid within the internal channel such that the float element seals the sensor opening of the sensor from the liquid.

In an embodiment, a sensor includes a sensor head assembly having a detector body, and a sensor cartridge held by the detector body of the sensor head assembly. The sensor cartridge includes a sensing element that is exposed by a sensing opening, and a sealing valve mounted to the detector body of the sensor head assembly. The sealing valve includes a housing having an internal channel. The housing is configured to be mounted to the detector body of the sensor head assembly and includes a housing opening that fluidly communicates with the internal channel for enabling a liquid to enter the internal channel. The sealing valve includes a float element configured to float along a surface of the liquid. The float element is held in the internal channel of the housing such that the float element is configured to move within the internal channel between an open position and a closed position. The float element is configured to close the sensor opening to the internal channel in the closed position. The sensor opening is open to the internal channel when the float element is in the open position. The float element is configured to rise with the surface of the liquid within the internal channel toward the closed position.

DETAILED DESCRIPTION

Figure 1:
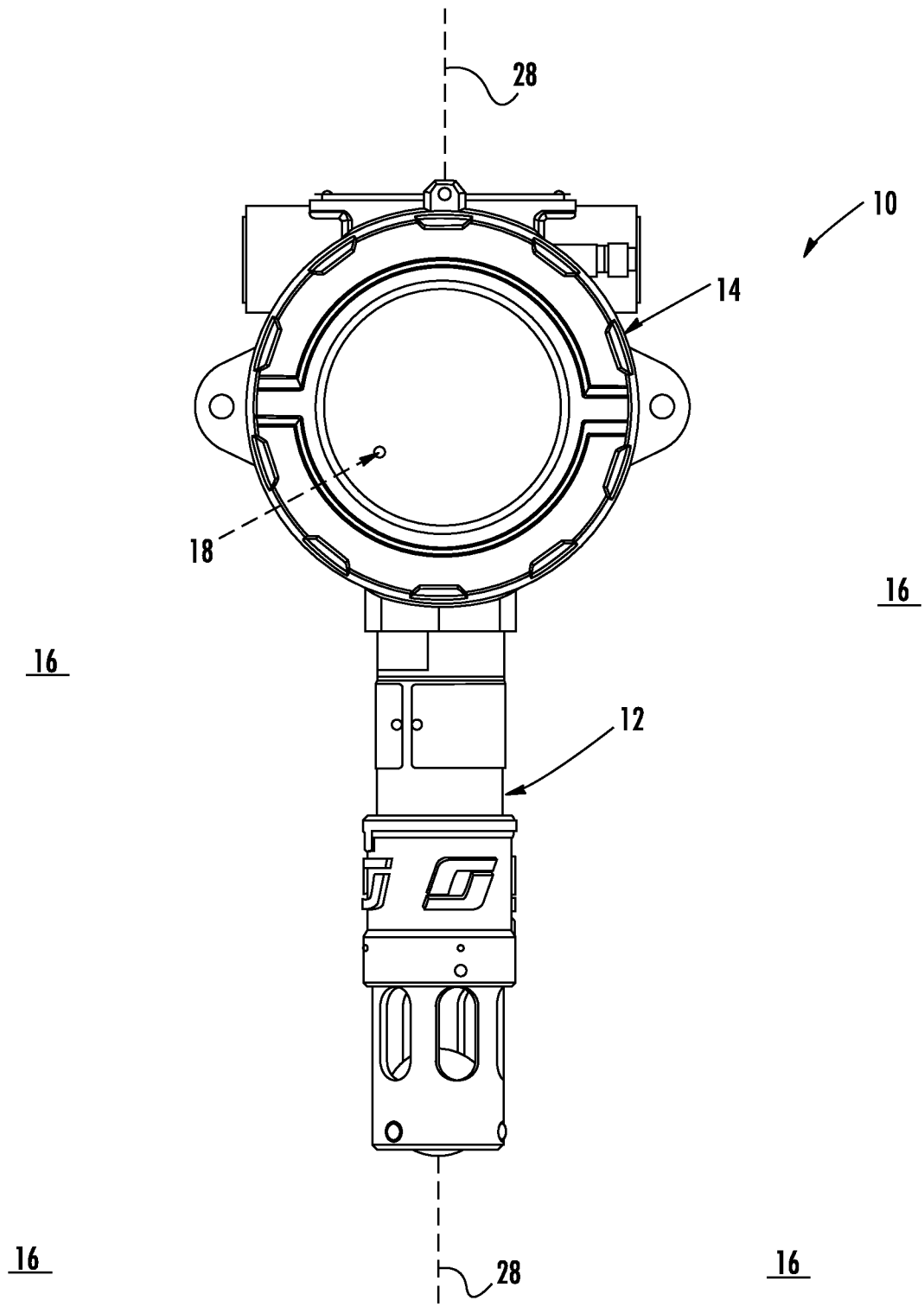
FIG. 1 is a plan view of an embodiment of a sensor assembly.

FIG. 1 is a plan view of an embodiment of a sensor assembly 10. The sensor assembly 10 includes a sensor 12 and a mounting structure 14. As shown in FIG. 1, the sensor 12 is mounted to the mounting structure 14 such that the sensor 12 is exposed within an environment 16 for sensing one or more parameters within the environment 16. The sensor 12 may be any type of sensor that is configured to sense any parameter(s). For example, in some embodiments, the sensor 12 is configured to detect the presence and/or amount of any substance (e.g., a vapor and/or a gas, such as, but not limited to, a volatile gas, a volatile vapor, a combustible gas, a combustible vapor, a toxic gas, a toxic vapor, and/or the like) within the environment 16. Examples of other parameters that may be sensed by the sensor 12 include, but are not limited to, pressure, density, temperature, relative humidity, and/or the like. The sensor 12 may be used in any application and the environment 16 may be any environment, such as, but not limited to, a sump area, a holding area, a well, and/or the like. In some embodiments, the environment 16 is a hazardous environment, such as, but not limited to, petroleum well, a power plant, a petroleum pipe system, and/or the like. For example, the sensor 12 may be used within a hazardous environment for detecting the presence and/or amount of a volatile, combustible, and/or toxic gas within the hazardous environment.

The mounting structure 14 supports the sensor 12 such that the sensor 12 is exposed within the environment 16 for performing sensing operations. The mounting structure 14 may include any structure, means, configuration, and/or the like that enables the mounting structure 14 to support the sensor 12 within the environment 16. In some embodiments, the mounting structure 14 is merely a panel and/or wall to which the sensor 12 is mounted, while in other embodiments the mounting structure 14 may include processing components, power supply components, communications components, and/or the like that support operation of the sensor 12. For example, the mounting structure 14 may hold one or more electrical power sources (not shown; e.g., a battery and/or the like) and/or one or more electrical power distribution components (not shown; e.g. electrical wires and/or cables, circuit boards, switches, relays, transformers, capacitors, voltage regulators, current regulators, and/or the like) for supplying electrical power to the sensor 12 to power operation of the sensor 12. The mounting structure 14 may hold one or more processing components (not shown; e.g., computers, processors, controllers, microprocessors, circuit boards, microcontrollers, memories, integrated circuits, and/or the like) that process signals from the sensor 12 that represent the parameter(s) sensed by the sensor 12. Processing of signals from the sensor 12 optionally includes data logging operations. In addition or alternative to the power supply component(s) and/or the processing component(s), the mounting structure 14 may hold one or more communication components (not shown; e.g., electrical wires and/or cables, circuit boards, other electrical pathways, switches, relays, communication nodes, and/or the like) that enables the sensor 12 to communicate with a remote location and/or other sensors. The remote location and/or the other sensors may contain one or more processing components and/or electrical power components that relate to operation of the sensor 12.

Optionally, the mounting structure 14 may include an interior chamber that is hermetically sealed to separate a volume of space within the mounting structure 14 from the environment 16. For example, in the illustrated embodiment, the mounting structure 14 is an explosion-resistant housing having an interior chamber 18 that holds one or more processing components, power supply components, and/or communication components that relate to operation of the sensor 12. The interior chamber 18 is separated from the environment 16 such that any combustion and/or explosion within the interior chamber 18 is less likely to extend into the environment 16. As such, any combustion and/or explosion that occurs within the interior chamber 18 is less likely to cause any substance within the environment to combust and/or explode. The illustrated embodiment of the mounting structure 14 may be commonly referred to as an "explosion-proof transmitter enclosure." Although described above as being an active sensor that requires a supply of electrical power to operate, the sensor 12 may be a passive sensor that does not require a supply of electrical power to operate.

Figure 2:
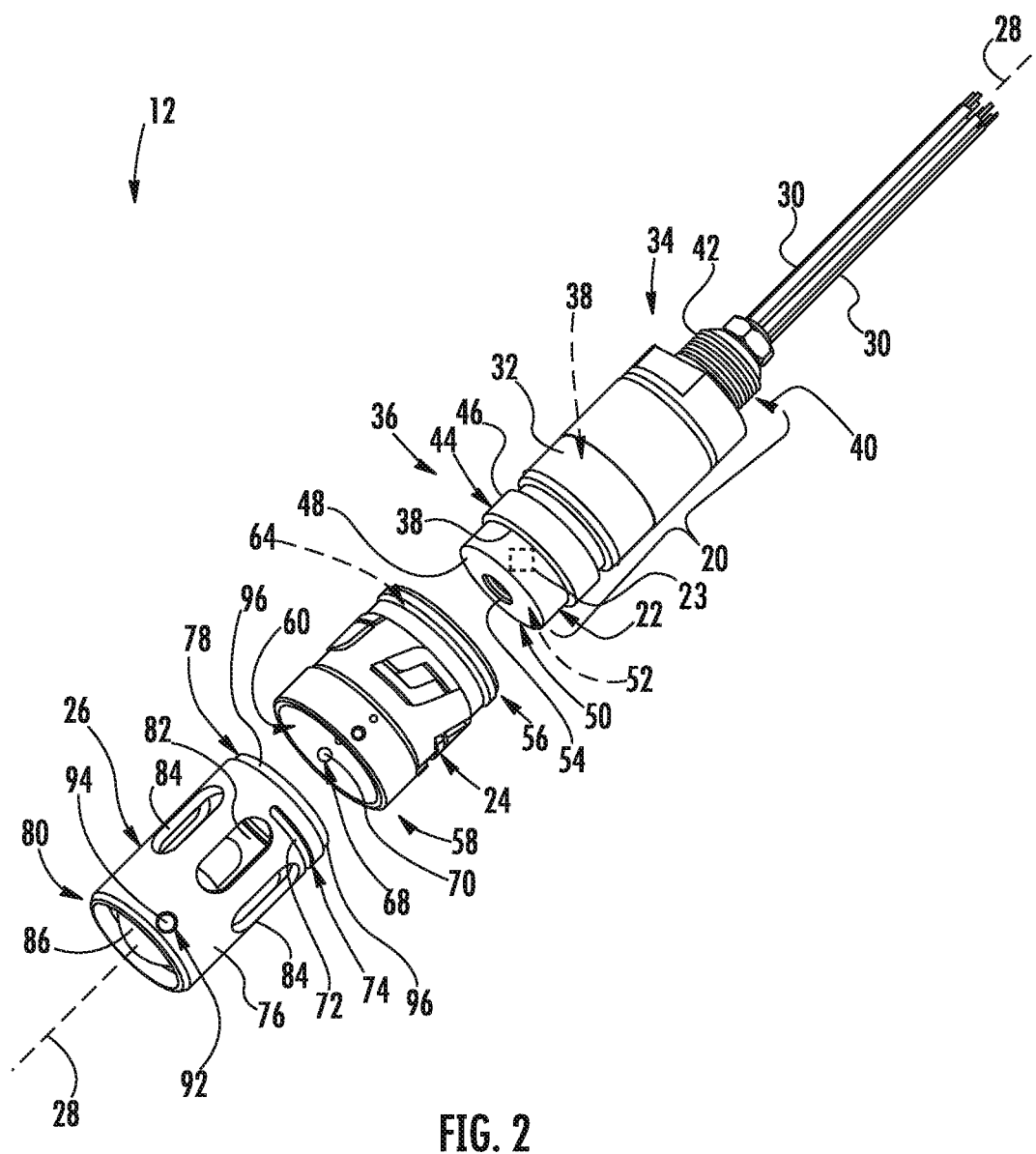
FIG. 2 is an exploded perspective view of an embodiment of a sensor of the sensor assembly shown in FIG. 1.

FIG. 2 is an exploded perspective view of an embodiment of the sensor 12 shown in FIG. 1. The sensor 12 includes a sensor head assembly 20, a sensor cartridge 22, a retaining cap 24, and a sealing valve 26. The sensor 12 is elongated and extends along a central longitudinal axis 28. When the sensor cartridge 22 is attached to the sensor head assembly 20 as shown in FIG. 2, the sensor cartridge 22 and the sensor head assembly 20 are electrically connected together. The sensor head assembly 20 is electrically connected to the mounting structure 14, the processing component(s), the power supply component(s), and/or the communication component(s) via one or more electrical wires 30 (which may or may not be grouped together in an electrical cable).

The sensor head assembly 20 includes a detector body 32. The detector body 32 extends a length along the central longitudinal axis 28 from an end 34 to an opposite end 36. The detector body 32 includes an internal channel 38 that extends through the detector body 32 along at least a portion of the length of the detector body 32. The internal channel 38 extends into the detector body 32 through the end 36 such that the end 36 is open to the internal channel 38.

The sensor head assembly 20 may include an attachment member 40 for mounting the sensor 12 to the mounting structure 14 (shown in FIG. 1). In the illustrated embodiment, the attachment member 40 includes a thread 42 for threadably connecting the sensor 12 to the mounting structure 14. But, in addition or alternatively to the thread 42, the attachment member 40 may use any other mounting strategy, such as, but not limited to, an adhesive, an interference fit, a snap-fit, a latch, a clip, a clamp, a threaded fastener, and/or the like. In the illustrated embodiment, the attachment member 40 is located at the end 34 of the detector body 32, however, the attachment member 40 may have any other location along the detector body 32.

The sensor head assembly 20 may include an attachment member 44 for mounting the retaining cap 24 to the detector body 32. The illustrated embodiment of the attachment member 44 includes a thread 46 that enables the retaining cap 24 to be mounted to the detector body 32 by being threadably connected to the detector body 32. In addition or alternatively to the thread 46, the attachment member 44 may use any other mounting strategy for mounting the retaining cap 24 to the detector body 32, such as, but not limited to, an adhesive, an interference fit, a snap-fit, a latch, a clip, a clamp, a threaded fastener, and/or the like. Although the attachment member 44 is shown as being formed at the end 36 of the detector body 32, the attachment member 44 may have any other location along the detector body 32.

The sensor cartridge 22 is held by the detector body 32 of the sensor head assembly 20, as shown in FIG. 2. The sensor cartridge 22 includes a cartridge housing 48 that includes an end 50 and an interior chamber 52. The sensor cartridge 22 includes a sensing element 23 that is held within the interior chamber 52 of the cartridge housing 48. The sensing element 23 is configured to sense one or more parameters from the environment 16 (shown in FIGS. 1, 3, and 4). The sensing element 23 may be any type of sensing element 23 that is configured to sense the parameter(s) in any manner. In the illustrated embodiment, the sensing element 23 is a diffusion type sensing element 23 that senses the parameter(s) through diffusion. The cartridge housing 48 includes a diffusion opening 54 that exposes the sensing element 23 to the environment 16 to enable the sensing element 23 to sense the parameter(s) through diffusion. Although shown as extending through the end 50 of the cartridge housing 48, the diffusion opening 54 may be positioned at any other location along the cartridge housing 54 that enables the sensing element 23 to sense the parameter(s). Although only one is shown, the cartridge housing 48 may include any number of diffusion openings 54. Any other type of sensing element 23 may be used in addition or in alternative to the diffusion type sensing element 23 described herein.

The retaining cap 24 extends a length along the central longitudinal axis 28 from an end 56 to an opposite end 58. The retaining cap 24 includes an interior passage 60 that extends through the length of the retaining cap 24. The retaining cap 24 is configured to be mounted to the detector body 32. When mounted to the detector body 32, the retaining cap 24 extends at least partially around the sensor cartridge 22 for protecting the sensor cartridge 22 from damage (e.g., impact damage).

The sensing element 23 of the sensor cartridge 22 is exposed to the environment 16 through the internal passage 60 of the retaining cap 24, which is open to the environment 16 at the end 58 of the retaining cap 24. A segment of the interior passage 60 defines a sensor opening 62 (shown in FIGS. 3 and 4) that exposes the sensing element 23 of the sensor cartridge 22 to the environment. The sensor opening 62 is aligned with the diffusion opening 54 for exposing the sensing element 23. The interior passage 60 optionally includes a screen 63 (shown in FIGS. 3 and 4) to facilitate preventing debris from entering the interior passage 60 and possibly fouling the sensing element 23. For example, the screen 63 may extend across the sensor opening 62. In some alternative embodiments, the detector body 32 and/or another component of the sensor 12 includes the sensor opening 62, for example the sensor opening 62 may be completely defined by the diffusion opening 54 (e.g., in embodiments wherein the retaining cap 24 is not included).

The retaining cap 24 includes an attachment member 64 for mounting the retaining cap 24 to the detector body 32. In the illustrated embodiment, the attachment member 64 includes a thread 66 (shown in FIGS. 3 and 4) that enables the retaining cap 24 to be mounted to the detector body 32 by threadably connecting the retaining cap 24 to the thread 46 of the detector body 32. Additionally or alternatively, the attachment member 64 may use any other mounting strategy for mounting the retaining cap 24 to the detector body 32, such as, but not limited to, an adhesive, an interference fit, a snap-fit, a latch, a clip, a clamp, a threaded fastener, and/or the like. Although the attachment member 64 is shown as being formed at the end 56 of the retaining cap 24, the attachment member 64 may have any other location along the retaining cap 24.

The retaining cap 24 includes an attachment member 68 for mounting the sealing valve 26 and/or one or more other accessories (not shown) to the sensor 12. Examples of other accessories include, but are not limited to, calibration adapters, water deluge guards, positive flow-through adapters, and/or the like. In the illustrated embodiment, the attachment member 68 includes pins 70 that are received within a groove (i.e., partial thread) 72 of a corresponding attachment member 74 of the sealing valve 26 to connect the attachment members 68 and 74 together with a partial-turn (i.e., bayonet) type connection. In addition or alternatively, any other type of connection may be used to mount the sealing valve 26 to the retaining cap 24. The attachment member 68 may include any number of the pins 70.

The sealing valve 26 is configured to be mounted to the detector body 32 of the sensor 12. Specifically, the sealing valve 26 includes a housing 76 that is configured to be mounted to the detector body 32 of the sensor 12 to mount the sealing valve 26 to the sensor 12. In the illustrated embodiment, the housing 76 is configured to be mounted to the retaining cap 24 to mount the sealing valve 26 to the detector body 32. Alternatively, the housing 76 is configured to be mounted directly to the detector body 32 to mount the sealing valve 26 to the sensor 12, for example in embodiments wherein the sensor 12 does not include the retaining cap 24. Although shown as being a discrete component from the retaining cap 24 and the detector body 32, the housing 76 of the sealing valve 26 may alternatively be integrally formed with the retaining cap 24 and/or the detector body 32 as a single, unitary body. As used herein, the housing 76 is considered to be "configured to be mounted" to the sensor 12 in embodiments wherein the housing 76 is integrally formed with the retaining cap 24 and/or the detector body 32 as a single, unitary body.

The housing 76 includes the attachment member 74 of the sealing valve 26, which in the illustrated embodiment cooperates with the attachment member 68 of the retaining cap 24 to mount the sealing valve 26 to the sensor 12. As discussed above, any other type of connection may be used in addition or alternative to the illustrated partial-turn (i.e., bayonet) type connection. Moreover, although the housing 76 includes the groove 72 and the retaining cap 24 includes the pins 70, in other embodiments the housing 76 may include the pins 70 and the retaining cap 24 may include the groove 72. Although shown as extending along an end 78 of the housing 76, the attachment member 74 may be positioned at any other location along the housing 76 that enables the sealing valve 26 to be mounted to the sensor 12.

Optionally, the sealing valve 26 is configured to be releasably mounted to the sensor 12. For example, in the illustrated embodiment, the partial turn type connection between the attachment members 68 and 74 provides a releasable (i.e., separable) connection between the housing 76 and the retaining cap 24. Other types of releasable connections may be additionally or alternatively used.

The housing 76 of the sealing valve 26 extends a length along the central longitudinal axis 28 from the end 78 to an opposite end 80. The housing 76 includes an internal channel 82 that extends through the housing 76 along at least a portion of the length of the housing 76. The internal channel 82 extends into the housing 76 through the end 78 such that the end 78 is open to the internal channel 82. In the illustrated embodiment, the end 80 is open to the internal channel 82, however in other embodiments the end 80 is closed to the internal channel 82. Each of the ends 78 and 80 may be referred to herein as an "open end".

The housing 76 includes one or more housing openings 84 that fluidly communicate with the internal channel 82 for enabling one or more liquids to enter the internal channel 82. Although six are shown, the housing 76 may include any number of the housing openings 84. Each housing opening 84 may include any shape in addition or alternative to the shapes shown herein.

Figure 3:
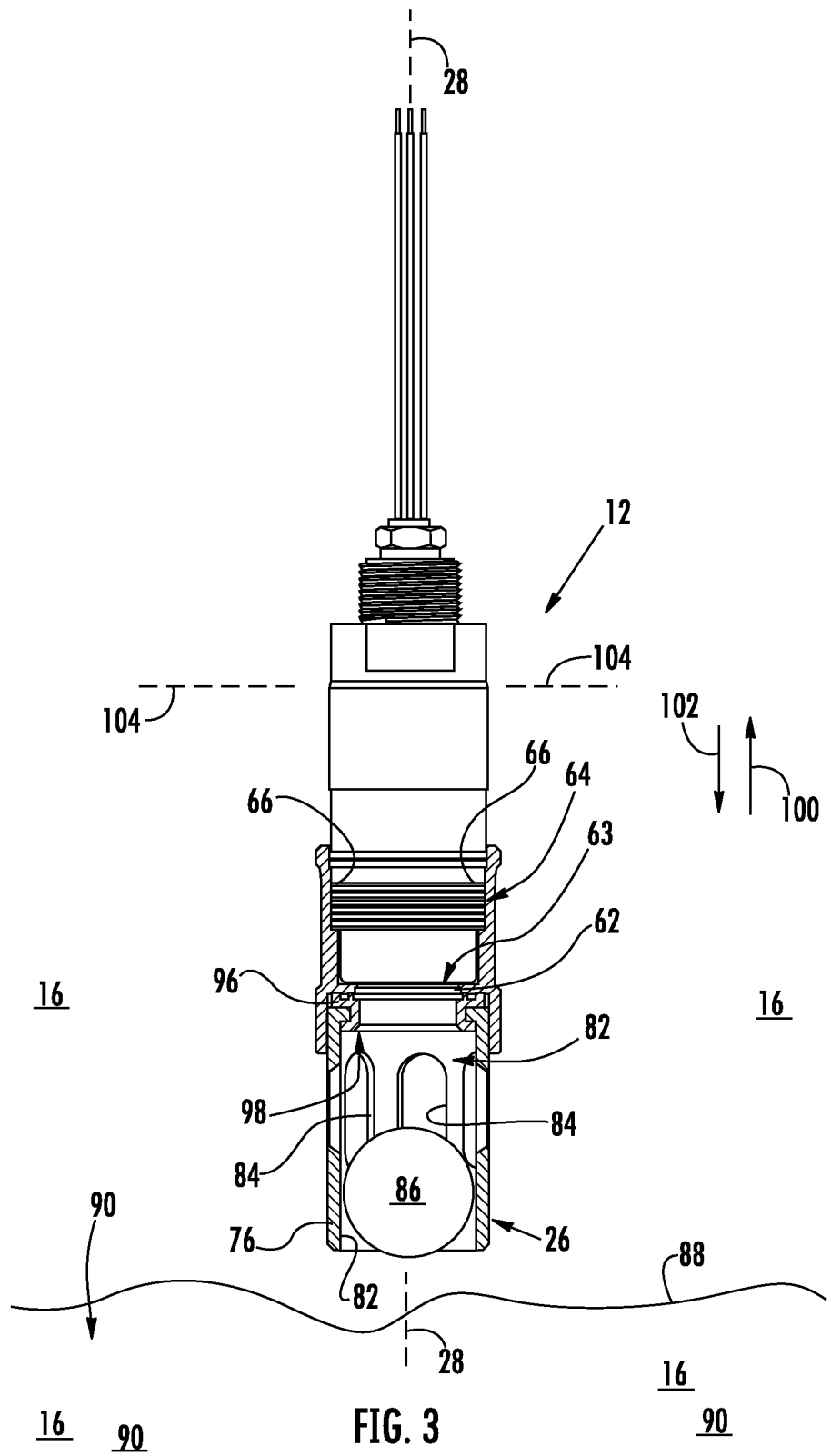
FIG. 3 is a perspective view illustrating a cross section of the sensor shown in FIG. 2 with an embodiment of a float element in a fully open position.
Figure 4:
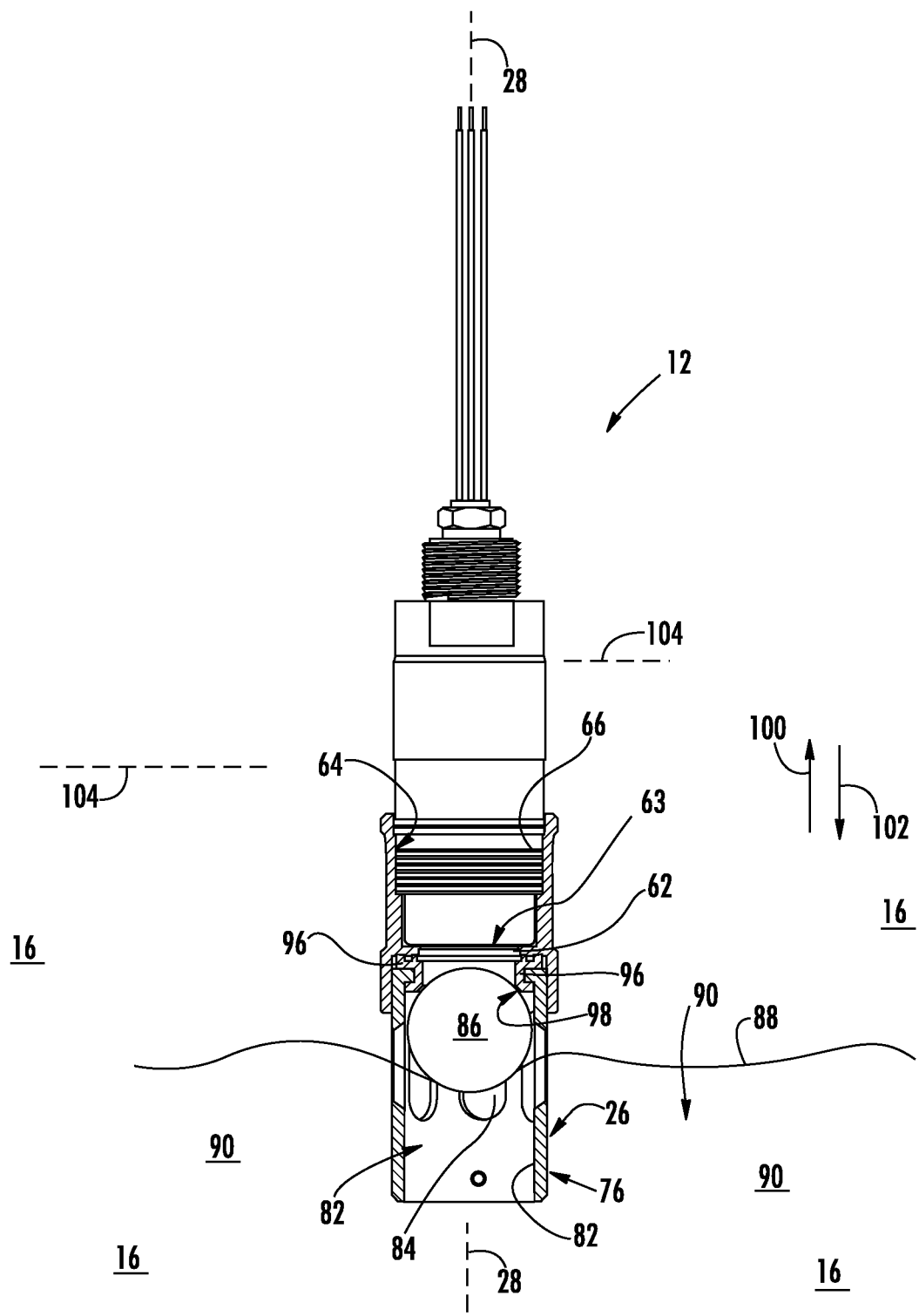
FIG. 4 is another perspective view of the sensor shown in FIGS. 2 and 3 illustrating the cross section of FIG. 3 with the float element in a closed position.

The sealing valve 26 includes a float element 86 that is configured to float along a surface 88 (shown in FIGS. 3 and 4) of a liquid 90 (shown in FIGS. 3 and 4). The float element 86 may be configured to float in any liquid(s) 90, such as, but not limited to, water, ground water, a corrosive liquid, a toxic liquid, an acidic liquid, a combustible liquid, a fuel, a petroleum based liquid, an oil, and/or the like. In the illustrated embodiment, the float element 86 includes a spherical shape. But, in addition or alternatively to the spherical shape, the float element 86 may include any other shape that enables the float element 86 to function as described and/or illustrated herein, such as, but not limited to, a parallelepiped shape, a shape having any number of sides greater than three, a wedge shape, a triangular shape, and/or the like.

The float element 86 is held within the internal channel 82 of the housing 76 such that the float element 86 is configured to rise with the surface 88 of the liquid 90 within the internal channel 82. The float element 86 is held in the internal channel 82 of the housing 76 such that the float element 86 is configured to move within the internal channel 82 between a closed position (shown in FIG. 4) and one or more open positions (a fully open position of the float element 86 is shown in FIG. 3). In other words, the float element 86 is held within the internal channel 82 such that the float element 86 is configured to move within the internal channel 82 toward and away from the sensor opening 62, as is better illustrated in FIGS. 3 and 4. In the closed position, the float element 86 is configured to close the sensor opening 62 to the internal channel 82 such that the float element 86 seals the sensor opening 62 from the liquid 90. In the open positions, the sensor opening 62 is open to the internal channel 82 such that the sensing element 23 is exposed to the environment 16 through the sensor opening 62.

The housing 76 optionally includes a retainment member 92 that is configured to permanently or releasably retain the float element 86 within the internal channel 82. In other words, the retainment member 92 is configured to permanently or releasably prevent the float element 86 from exiting the internal channel 82 through the end 80 of the housing 76. In the illustrated embodiment, the retainment member 92 includes resiliently retractable pins 94 that engage in physical contact with the float element 86 to retain the float element 86 within the internal channel 82. In addition or alternatively, the retainment member 92 may include any other structure that enables the retainment member 92 to function as described and/or illustrated herein. The retainment member 92 may include any number of the pins 94.

The sealing valve 26 optionally includes a gasket 96 held within the internal channel 82 of the housing 76. As should be apparent from FIG. 2 but is better seen in FIGS. 3 and 4, the gasket 96 extends between the float element 86 and the sensor opening 62. As will be described in more detail, the float element 86 is configured to engage in sealing engagement with the gasket 96 in the closed position to close the sensor opening 62 to the internal channel 82. The gasket 96 may be fabricated from any material(s) that enable the gasket 96 to engage in sealing engagement with the float element 86, such as, but not limited to, an elastomeric material (e.g., rubber) and/or the like.

Optionally, the gasket 96 includes a tapered seat 98 (shown in FIGS. 3 and 4). The float element 86 is configured to be seated (i.e., received) in the tapered seat 98 in the closed position, which may facilitate creating the sealing engagement between the float element 86 and the gasket 96. The tapered seat 98 may have any tapered shape that enables the gasket 96 to function as described and/or illustrated herein.

FIG. 3 is a perspective view illustrating a cross section of the sensor 12 with an embodiment of the float element 86 in the fully open position. FIG. 4 is another perspective view of the sensor 12 illustrating the cross section of FIG. 3 with the float element 86 in the closed position. As shown in FIG. 3, the housing 76 is mounted to the sensor 12 such that the internal channel 82 fluidly communicates with the sensor opening 62. As can also be seen in FIG. 3, the gasket 96 extends along the central longitudinal axis 28 between the float element 86 and the sensor opening 62.

The float element 86 is shown in FIG. 3 in the fully open position wherein the float element 86 does not completely obstruct (i.e., close) the sensor opening 62 such that the sensing element 23 of the sensor 12 is exposed to the environment 16. In other words, when the float element 86 is in the fully open position shown in FIG. 3, the sensor opening 62 is open to the internal channel 82 of the housing 76 such that the sensing element 23 is exposed to the environment 16 through the sensor opening 62 and the housing openings 84.

As described above, the float element 86 moves within the internal channel 82 (and along the central longitudinal axis 28) toward and away from the sensor opening 62, which is indicated by the respective arrows 100 and 102. The float element 86 is configured to move in the direction of the arrow 102 by gravity. The float element 86 is configured to be held in the fully open position by gravity. The fully open position of the float element 86 shown in FIG. 3 represents the furthest position of the float element 86 from the sensor opening 62. The closed position of the float element 86 shown in FIG. 4 represents the closest position of the float element 86 to the sensor opening 62. As should be understood from FIGS. 3 and 4, in all positions of the float element 86 wherein the float element 86 is further away from the sensor opening 62 than the closed position (e.g., all positions of the float element 86 wherein the float element 86 is not sealingly engaged with the gasket 96), the sensing element 23 is exposed to the environment 16 through the sensor opening 62 and the housing openings 84.

The environment 16 includes the liquid 90, which may be any liquid(s) 90, such as, but not limited to, water, ground water, a corrosive liquid, a toxic liquid, an acidic liquid, a combustible liquid, a fuel, petroleum based liquid, an oil, and/or the like. As the level of the surface 88 of the liquid 90 rises, the float element 86 floats on the surface 88 and rises with the surface 88 within the internal channel 82 toward the closed position. When the level of the surface 88 raises sufficiently high, the float element 86 rises (in the direction of the arrow 100) to the closed position shown in FIG. 4. In the closed position, the float element 86 is engaged in sealing engagement with the gasket 96 (e.g., is seated within the tapered seat 98 of the gasket 96) to thereby close the sensor opening 62 to the internal channel 82. The float element 86 thereby seals the sensor opening 62 from the liquid 90 in the closed position. In other words, in the closed position, the float element 86 completely obstructs the sensor opening 62 such that the sensing element 23 of the sensor 12 is not exposed to the liquid through the sensor opening 62. The sealing valve 26 thereby protects the sensing element 23 of the sensor 12 from damage caused by exposure to the liquid 90.

Although the sensor 12 is shown as being mounted to the mounting structure (shown in FIG. 1) such that the sensor 12 is oriented approximately vertical (e.g., approximately perpendicular to the horizontal axis 104 shown in FIGS. 3 and 4), it should be understood that the sensor 12 may be oriented such that the central longitudinal axis 28 is oriented at any non-horizontal angle (i.e., at any orientation that is non-parallel to the horizontal axis 104) that enables the sealing valve 26 to function as described and/or illustrated herein.

As used herein, an element or step recited in the singular and proceeded with the word "a" or "an" should be understood as not excluding plural of said elements or steps, unless such exclusion is explicitly stated. Furthermore, references to "one embodiment" or "an embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112, sixth paragraph, unless and until such claim limitations expressly use the phrase "means for" followed by a statement of function void of further structure.

What is claimed is:

1. A sealing valve for a sensor that includes a retaining cap and a diffusion opening that exposes a portion of the sensor to an environment, the sealing valve comprising:
    a housing having a first end, a second end opposite the first end, and an internal channel therebetween, the first end of the housing being configured to be mounted to the sensor such that the internal channel fluidly communicates with the diffusion opening of the sensor, the second end of the housing comprising a housing opening that is directly open to the environment and fluidly communicates with the internal channel for enabling a liquid to enter the internal channel, the housing including an attachment member that includes a pin to mount the housing to the retaining cap;
    a spherical float element configured to float in the liquid, the spherical float element being held in the internal channel of the housing such that the spherical float element is configured to move within the internal channel toward and away from the diffusion opening, the spherical float element being configured to rise with the surface of the liquid within the internal channel such that the spherical float element seals the diffusion opening of the sensor from the liquid; and
    a gasket held within the internal channel of the housing such that the gasket extends between the spherical float element and the diffusion opening, the spherical float element being in direct contact with the gasket when the spherical float element seals the diffusion opening from the liquid.

2. The sealing valve of claim 1, wherein the housing is configured to be mounted to the sensor using a partial-turn connection.

3. The sealing valve of claim 1, wherein the spherical float element is configured to move within the internal channel between an open position and a closed position.

4. The sealing valve of claim 3, wherein the gasket includes a tapered seat, the spherical float element being seated in the tapered seat in the closed position to close the diffusion opening to the internal channel.

5. The sealing valve of claim 3, wherein the spherical float element is configured to be at least one of moved toward and held in the open position by gravity.

6. A sensor comprising:
    a sensor head assembly comprising a detector body;
    a sensor cartridge held by the detector body of the sensor head assembly, the sensor cartridge comprising a diffusion opening, a portion of the sensor cartridge being exposed by the diffusion opening to an environment;
    a retaining cap mounted to the detector body; and
    a sealing valve mounted to the detector body of the sensor head assembly, the sealing valve comprising:
        a housing having a first end, a second end opposite the first end, and an internal channel therebetween, the first end of the housing being configured to be mounted to the detector body of the sensor head assembly, the second end of the housing comprising a housing opening that is directly open to the environment and fluidly communicates with the internal channel for enabling a liquid to enter the internal channel, the housing including an attachment member that includes a pin to mount the housing to the retaining cap;
        a float element configured to float along a surface of the liquid, the float element being held in the internal channel of the housing such that the float element is configured to move within the internal channel between an open position and a closed position, the diffusion opening being open to the internal channel when the float element is in the open position, the float element being configured to rise with the surface of the liquid within the internal channel toward the closed position; and
        a gasket comprising a tapered seat, the float element being seated in the tapered seat in the closed position to close the diffusion opening to the internal channel.

7. The sensor of claim 6, wherein the retaining cap comprises a sensor opening and an internal passage in communication with the sensor opening, the portion of the sensor cartridge being exposed through the retaining cap internal passage.

8. The sensor of claim 6, wherein the housing of the sealing valve is mounted to the detector body of the sensor head assembly by being mounted to the retaining cap.

9. The sensor of claim 6, wherein the float element is configured to be at least one of moved toward and held in the open position by gravity.

10. The sensor of claim 6, wherein the float element is a spherical float element.

* * * * *